United States Patent
Auerbach et al.

(10) Patent No.: US 9,155,567 B2
(45) Date of Patent: Oct. 13, 2015

(54) POLYAXIAL PEDICLE SCREW AND FIXATION SYSTEM KIT COMPRISING THE SCREW

(75) Inventors: Joshua D. Auerbach, Brooklyn, NY (US); Zsolt Fekete, Bremen (DE); Meinrad Fiechter, Lugano (CH); Christoph E. Heyde, Leipzig (DE); Francesco Siccardi, Vico Morcote (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 504 days.

(21) Appl. No.: 13/426,214

(22) Filed: Mar. 21, 2012

(65) Prior Publication Data
US 2012/0245640 A1    Sep. 27, 2012

(30) Foreign Application Priority Data
Mar. 22, 2011   (EP) .................................... 11159254

(51) Int. Cl.
*A61B 17/70* (2006.01)
(52) U.S. Cl.
CPC ......... *A61B 17/7035* (2013.01); *A61B 17/7037* (2013.01); *A61B 17/7082* (2013.01)
(58) Field of Classification Search
CPC .............. A61B 17/708; A61B 17/7032; A61B 17/7037; A61B 17/7035; A61B 17/7074; A61B 17/7085; A61B 17/7086; A61B 17/7091; A61B 17/8685
USPC .......................... 606/264–279, 86 A, 305–308
See application file for complete search history.

(56) References Cited

U.S. PATENT DOCUMENTS

| 5,443,467 | A | 8/1995 | Biedermann et al. |
| 5,672,176 | A | 9/1997 | Biedermann et al. |
| 5,681,319 | A | 10/1997 | Biedermann et al. |
| 6,063,089 | A | 5/2000 | Errico et al. |
| 6,063,090 | A | 5/2000 | Schlapfer |
| 7,223,268 | B2 | 5/2007 | Biedermann |
| 2003/0167058 | A1 | 9/2003 | Shluzas |
| 2006/0173454 | A1* | 8/2006 | Spitler et al. ...................... 606/61 |
| 2008/0045953 | A1* | 2/2008 | Garamszegi ...................... 606/61 |
| 2010/0160977 | A1 | 6/2010 | Gephart et al. |
| 2011/0098755 | A1* | 4/2011 | Jackson et al. ................. 606/305 |
| 2011/0160778 | A1* | 6/2011 | Elsbury ......................... 606/305 |
| 2012/0143266 | A1* | 6/2012 | Jackson et al. ................. 606/328 |
| 2013/0131730 | A1* | 5/2013 | Jackson et al. ................. 606/278 |

FOREIGN PATENT DOCUMENTS

WO    WO 2012/064360 A1 *  5/2012    ............. A61B 17/86

* cited by examiner

*Primary Examiner* — Eduardo C Robert
*Assistant Examiner* — Michelle C Eckman
(74) *Attorney, Agent, or Firm* — Allen, Dyer, Doppelt, Milbrath & Gilchrist, P.A.

(57) ABSTRACT

A polyaxial pedicle screw may include a receiving head having a transversal U-shaped passage, and a shank having a threaded portion external to the receiving head, and a bulging end rotatable housed within the receiving head. The polyaxial pedicle screw may include a locking insert housed within the receiving head and matable with the bulging end, for locking it into position, and a set-screw engaged in the distal aperture for locking a connecting rod received within the transversal U-shaped passage. The receiving head of the polyaxial screw may include a lateral aperture, the lateral aperture exposing a contact surface of the locking insert in such a way that external pressing component can act on the contact surface to maintain the locking insert into its locking position.

21 Claims, 7 Drawing Sheets

POLYAXIAL PEDICLE SCREW AND FIXATION SYSTEM KIT COMPRISING THE SCREW

FIELD OF THE INVENTION

The present invention relates to the general field of orthopedic surgical implants, more specifically, a polyaxial pedicle screw being part of a pedicle screw fixation system, used in the field of surgical spine treatment.

BACKGROUND OF THE INVENTION

Surgical techniques for the treatment of spinal injuries or deformities are usually aimed at joining together two or more vertebrae of the spine, through a process that is called spinal fusion. A possible approach to spinal fusion adopts a fixation system that is anchored to the spine by way of orthopedic screws implanted into the pedicles of two or more subsequent vertebrae. The single screws are connected together by means of rigid or semi-rigid rods, which are conveniently housed within a transversal hole provided in the screw head.

However, due to the irregularity of bone anatomy, it is unlikely that once the screws have been implanted into the spine pedicles, their heads will be properly aligned for rod insertion. Hence, in order to facilitate the insertion of the rod, the screws are usually provided with a head that is freely rotatable with respect to their shank.

Screws of this type, named polyaxial screws, present a threaded shank with a bulging end that rotates in a socket-like cavity provided in the head. The upper part of the socket-like cavity is defined by a locking insert which is suitable to clamp the bulging end once the appropriate orientation of the shank has been set. The transversal hole for housing the connecting rod is arranged above the socket-like cavity, and a set-screw is provided above in order to clamp the rod into position. In typical polyaxial pedicle screws, such as the one disclosed in U.S. Pat. No. 5,672,176, the locking action of the set-screw determines the locking of both the connecting rod and the shank orientation, since the pressure applied by the set-screw is transmitted through the connecting rod to the locking insert.

However, such an arrangement may oblige the surgeon to insert the connecting rod while the screw head is freely rotatable with respect to the shank, which may be prejudicial to an optimal placement of the fixation system. As will be appreciated by those skilled in the art, spinal surgery, especially when adopting minimal invasive techniques, may be challenging and may be important to provide freedom of placement of the fixation systems together with ease of intervention.

An approach to the above-addressed issue is disclosed in U.S. Pat. No. 5,443,467, which discloses a peripherally threaded locking insert engaging with an internal threaded surface of the screw head. The shank orientation may thus be locked separately by the locking insert alone. However, such an approach does not allow the surgeon to correct the shank orientation during or after insertion of the connecting rod, since he would be unable to loosen the locking insert when the rod is placed upon it.

A different approach is disclosed in U.S. Pat. No. 7,223,268 and U.S. Pat. No. 6,063,090. These polyaxial screws have two concentric inner and outer upper set-screws: the outer one is intended to act on a portion of the locking insert, tightening it into position independently from the connecting rod, which is clamped by the inner one. However, the presence of the outer set-screw prevents insertion of the connecting rod from above, and as a consequence, the surgeon cannot lock the relative orientation of the shank before rod insertion in minimal invasive surgery.

Another approach is disclosed in U.S. Pat. No. 5,681,319, wherein a dedicated instrument is employed to keep the locking insert in clamping position during the setting of the connecting rod. However, this instrument has to be removed before insertion of the set-screw clamping the rod, once again limiting the surgeon's freedom in tightening and loosening the elements while looking for the best possible arrangement for the fixation system.

Another approach is disclosed in U.S. Pat. No. 6,063,089. This polyaxial screw has, a head having a side arm for the housing and separate locking of the connecting rod. However, such an arrangement may significantly increase the lateral profile of the fixation system, and may not suitable for traditional surgery techniques. Moreover, the position of the rod being off-set from the screw axis, the screw is also unsuitable for minimal invasive and deformity correction surgeries.

SUMMARY OF THE INVENTION

In view of the foregoing, an object is to provide a polyaxial pedicle screw allowing separate locking of the shank orientation while providing an approach to the drawbacks discussed above.

Another object of the present invention is that of allowing the surgeon to lock the relative orientation of the shank before rod insertion in minimal invasive surgery and/or deformative correction.

A polyaxial pedicle screw of the type may include a receiving head longitudinally extending from a proximal aperture to a distal aperture, the receiving head comprising a transversal U-shaped passage, opening on the periphery of the distal aperture. The screw may include a shank traversing the proximal aperture, having a threaded portion external to the receiving head and a bulging end rotatable housed within the receiving head, a locking insert housed within the receiving head and matable with the bulging end, the locking insert being movable into a locking position wherein it locks the relative movement of the bulging end with respect to the receiving head, a fixing device engaged in the distal aperture for locking a connecting rod received within the transversal U-shaped passage. The receiving head may present at least one lateral aperture, the lateral aperture exposing a contact surface of the locking insert in such a way that external pressing means or action can act on the contact surface to maintain the locking insert in its locking position.

Thus the external pressing action can act without hindering access to the U-shaped passage, and the insertion of the connecting rod may be performed without restrictions, independently from the locking of the shank orientation and independently from the screw placement.

The lateral apertures may advantageously be two lateral apertures defined by a through bore diametrically traversing the receiving head. Moreover, the locking insert may be housed within the through bore.

In particular, the locking insert may exhibit an elongated shape with two lateral arms extending through the lateral apertures, but without projecting out of the receiving head, the distal sides of the lateral arms defining the contact surface. In this embodiment, the lateral apertures may advantageously restrain the motion of the lateral arms of the locking insert in a distal direction.

Also, the receiving head may comprise two (or more) lateral longitudinal grooves opening on the through bore, the lateral longitudinal grooves defining longitudinal paths for the external pressing action. In such a way, the external pressing action extending through the longitudinal grooves may advantageously contact the lateral arms of the locking insert without projecting from the cross-section of the device, allowing minimally invasive techniques to be employed. The lateral arms may even have lateral extensions projecting out of the receiving head, but what may be helpful is that the distal sides of these lateral arms may offer a contact surface for the external pressing action.

The through bore defining the lateral apertures may preferably extend along an orthogonal axis with respect to the U-shaped passage. Possibly, the through bore is also proximally offset with respect to the passage.

In order to allow stable positioning of the external pressing action with respect to the receiving head, the head may comprise a plurality of formations intended for engagement of a dedicated instrument featuring the external pressing action. In particular, the formations may be indentations presented on the bevelled edges of a lateral periphery of the receiving head. The contact surface of the locking insert may be substantially flat or alternatively slightly concave.

An approach to the above-mentioned technical problem may include a fixation system kit comprising at least one polyaxial pedicle screw as described above, at least a connecting rod adapted to be housed within the transversal U-shaped passage, and at least an instrument comprising external pressing means or an action intended to act on the contact surface. The instrument may comprise lateral prongs able to connect with the receiving head of the polyaxial pedicle screw, the external pressing action being defined by pressing arms slidably mounted with respect to the lateral prongs. The lateral prongs may comprise internally projecting pins intended to cooperate with indentations on the receiving head to secure a connection between the two elements.

Further presents and advantages of the polyaxial pedicle screw and fixation system kit according to the invention shall be made clearer by the description, given below, of a specific embodiment described by way of non-limiting example with reference to the accompanying drawings.

DETAILED DESCRIPTION OF THE PREFERRED EMBODIMENTS

Figure 1:
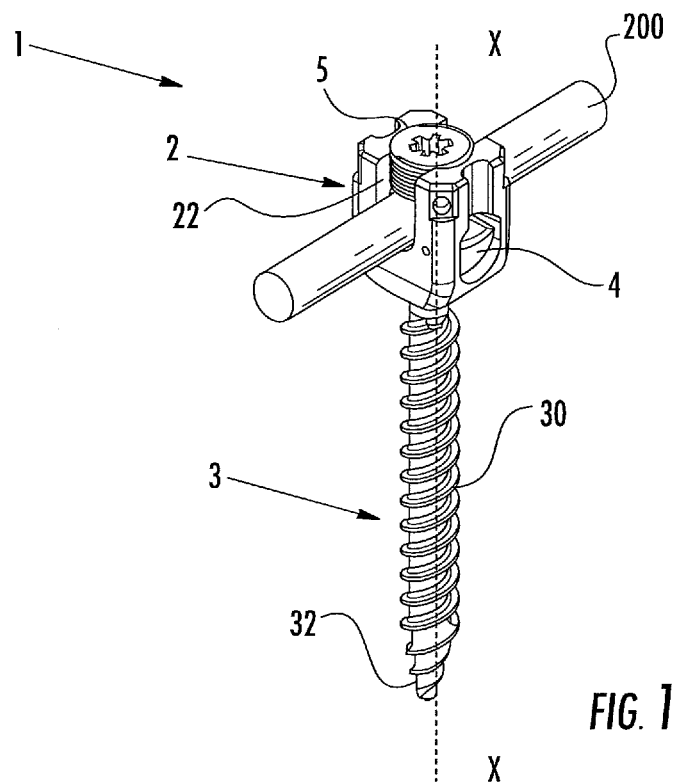
FIG. 1 shows a perspective view of a polyaxial pedicle screw, according to the present invention.
Figure 2:
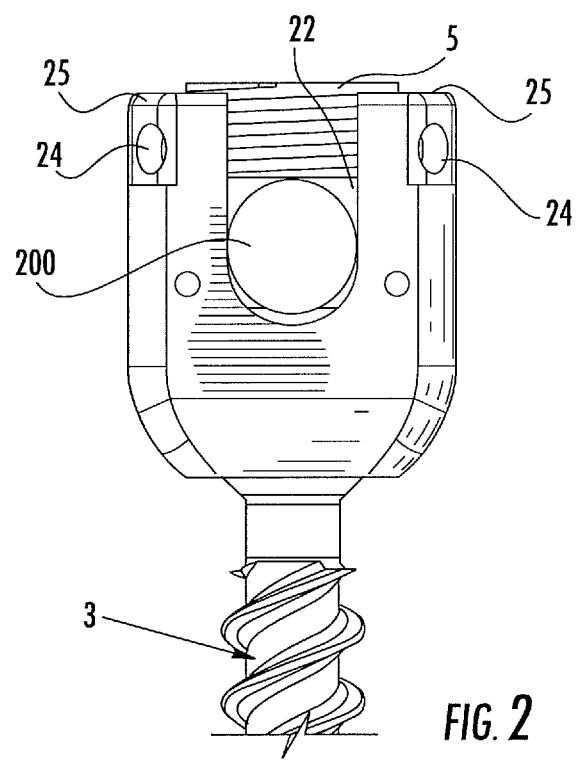
FIG. 2 shows a side view of the polyaxial pedicle screw in FIG. 1.
Figure 3:
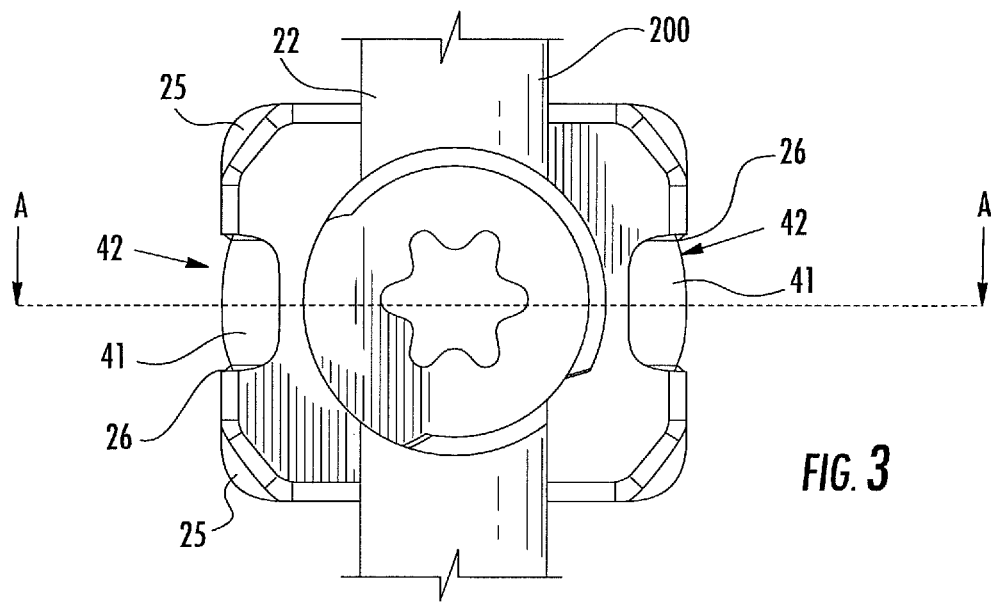
FIG. 3 shows a top view of the polyaxial pedicle screw in FIG. 1.
Figure 4:
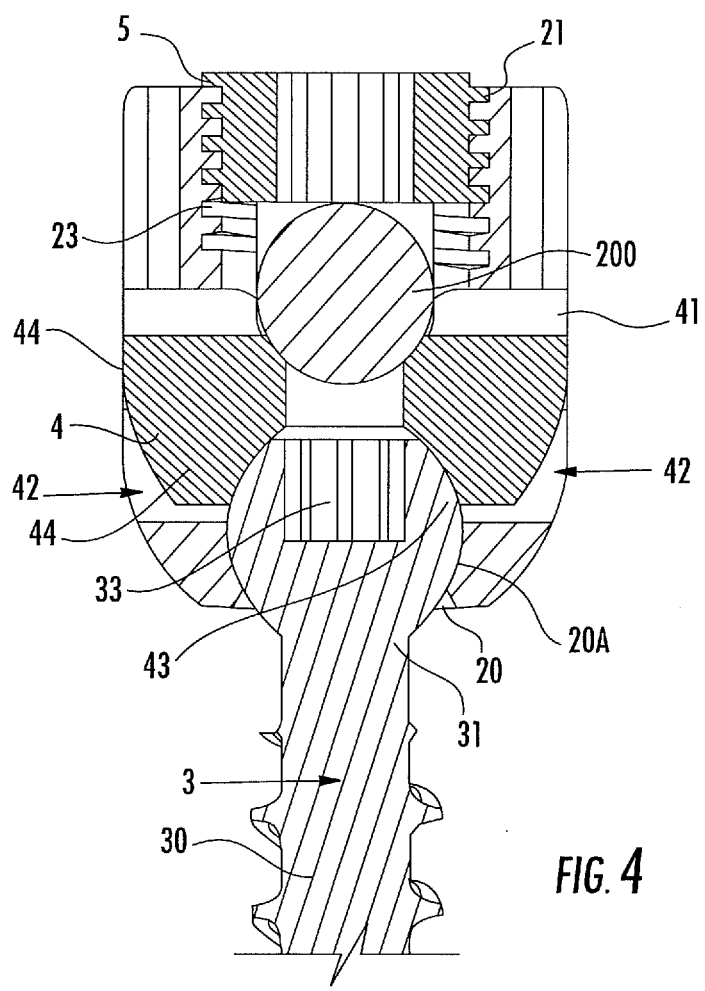
FIG. 4 shows a cross-sectional view of the polyaxial pedicle screw along a cross-section plane "A-A" identified in FIG. 3.
Figure 5:
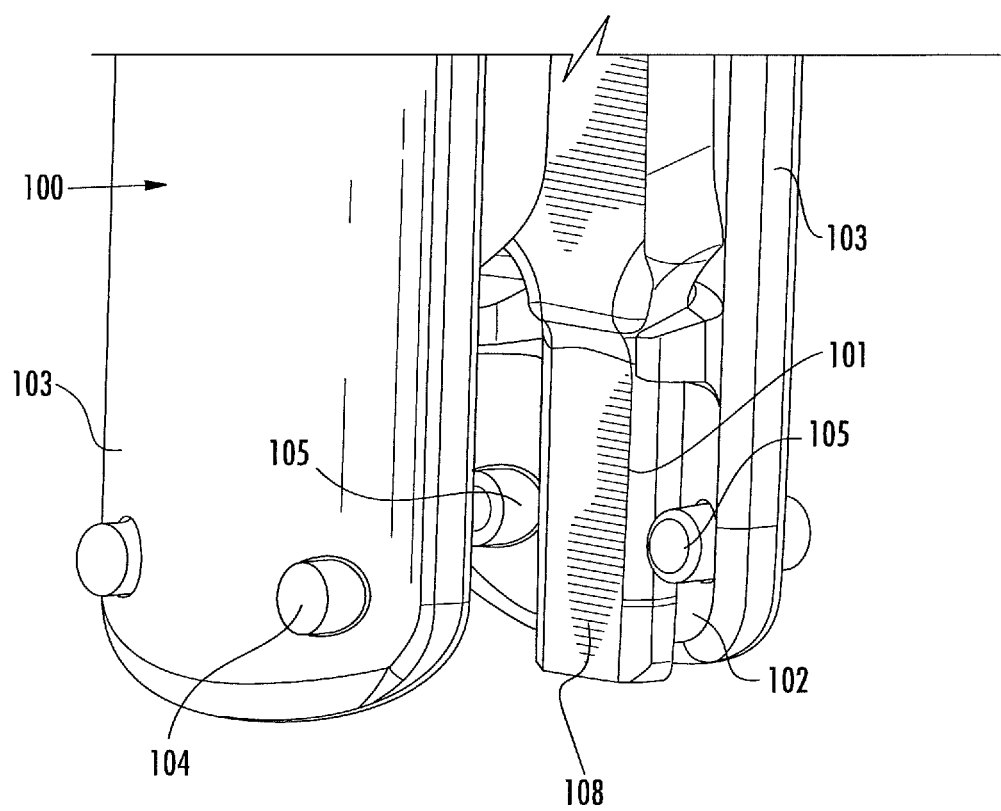
FIG. 5 shows a perspective view of the tip of an instrument adapted to act on the polyaxial pedicle screw, according to the present invention.
Figure 6:
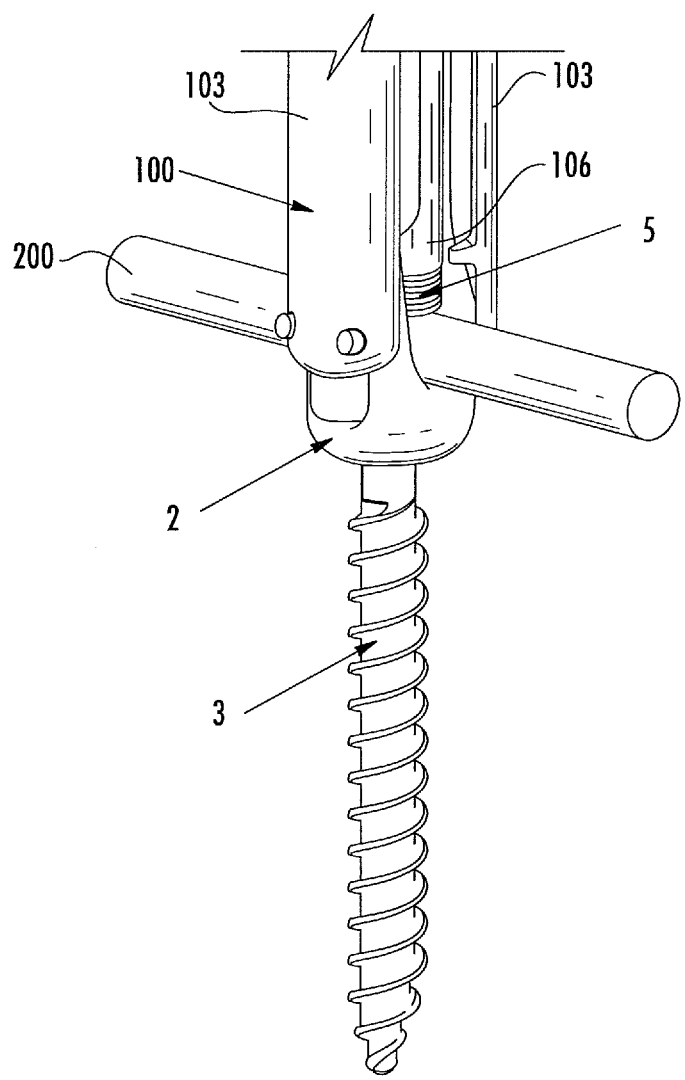
FIG. 6 shows a perspective view of the polyaxial pedicle screw according to the present invention connected to the instrument tip in FIG. 5.

Referring to FIGS. 1-4, a polyaxial pedicle screw 1 is illustrated according to the present invention. A plurality of such screws 1, along with connecting rods 200, form a fixation system for spinal surgery, which may be sold in a kit together with a locking instrument 100 as depicted in FIGS. 5-6. The polyaxial pedicle screw 1 comprises a shank 3 having a threaded portion 30 and a bulging end 31. The screw 1 may be cannulated or fenestrated without departing from the principles of the present invention. The screw may even be conical or straight and may be coated with an appropriate coating according to the application purposes.

The threaded portion 30, provided with a single or multiple lead threading and ending with a tip 32, is adapted for insertion and secure anchorage in the vertebral pedicle of a patient. In one embodiment, a dual lead thread is provided. The bulging end 31 has a substantially spherical shape, with a flat distal end featuring a socket 33 able to mate with an appropriate wrench. In other embodiments, alternative shapes of the bulging end 31 may be adopted. For example, the bulging end 31 may have a partially spherical shape or a shape that allows pivoting inside a corresponding hosting seat.

The polyaxial pedicle screw 1 also comprises a receiving head 2, which acts as a connecting element between the above mentioned shank 3 and a connecting rod 200, which in turn is intended to connect the polyaxial screw to one or more other screws implanted in the pedicles of neighboring vertebrae to be fused together. The rod 200 may be substantially rigid if realized by a metal alloy or flexible if realized by a synthetic plastic material such as for instance PEEK.

The receiving head 2 is a hollow structure, extending along a longitudinal axis x from a circular proximal aperture 20 to a distal aperture 21. It should be noted that the terms proximal and distal are used in the present document to identify the relative distance between the pedicle and the parts forming the device described. Hence, the proximal aperture is intended to lie closer to the pedicle, while the distal aperture will be farther from it, when the pedicle screw is correctly implanted in a patient.

The proximal aperture 20 is traversed by the shank 3. Since the diameter of the proximal aperture 20 is smaller than the diameter of the bulging end 31 of the shank 3, the end is retained within the hollow body of the receiving head 2, forming substantially a ball-and-socket joint 20A which allows uni-planar or poly-axial orientation of the shank 3 with respect to the receiving end. A uni-planar screw can be angulated in only one direction. As mentioned before, the shape of the bulging end 31 allows the shank 3 to be oriented according to the needs since the bulging end is rotatable hosted inside the hollow body of the receiving head 2. It should be noted that it is possible to introduce the tip of a wrench from the distal aperture and to engage the socket 33 of the bulging end 31, thus allowing screwing and unscrewing of the shank 3 from a patient's pedicle vertebra body.

A locking insert 4 is housed within the receiving head 2, and slidably movable along the longitudinal axis x of the device. The locking insert 4 presents a mating surface 43 which is substantially spherical on its proximal side and is faced toward the proximal aperture 20. The surface is intended to mate with the distal portion of the bulging end 31 of the shank, so that the locking insert 4 may lock the relative movement of the bulging end 31 with respect to the receiving head 2 of the device when maintained in a locking position, i.e. pressed toward the proximal end of the receiving head 2. The locking insert 4 may even be secured, for instance by a transverse pin. This would prevent disassembling of the components. The receiving head 2 is diametrically traversed by a through bore made right above the level of its proximal end. The through bore exhibits a cross-section roughly shaped like a round-edged square, and defines two lateral apertures 42 of the receiving head 2.

In other embodiments, other different and alternative shapes may be adopted without departing from the principle of the present invention. The locking insert 4 is housed within the diametrical through bore, exhibiting an elongated shape with two lateral arms 44 extending through the lateral apertures 42, without projecting out of the body of the receiving head. It should be noted that the lateral apertures 42 guide the sliding motion of the locking insert 4, and that the abutment of the lateral arms 44 against the periphery of the apertures conveniently restrains movement in a distal direction. The locking insert 4 presents a central hole in order to allow a wrench tip to reach the socket 33 of the bulging end 31 from the distal aperture 21.

The distal sides of the two lateral arms 44 of the locking insert 4 are conveniently flat or slightly concave, and define two contact surfaces 41 that are faced toward the distal aperture 21 and substantially opposed to the mating surface 43. The purpose of these two contact surfaces will be explained in a following section of the present description.

The receiving head 2 of the polyaxial pedicle screw 1 also presents a transverse U-shaped passage 22, the purpose of which is to receive the connecting rod 200 intended to bridge the polyaxial pedicle screw 1 to a neighboring one. The U-shaped passage 22 opens on the periphery of the previously defined distal aperture 21, and is in fact defined by two U-shaped notches provided on opposite sides of the lateral rim surrounding the distal aperture 21.

The U-shaped passage 22 and the lateral apertures 42 extend along two orthogonal axes that are offset in the longitudinal direction. Indeed, the proximal extremity of the U-shaped passage 22 is set distally with respect to the proximal extremity of the above-mentioned lateral apertures 42, but proximally with respect to the distal extremity of the apertures 42.

The internal surface of the lateral rim surrounding the distal aperture 21 presents a partial thread 23, and fixing means or set-screw 5 is predisposed to engage with the partial thread 23 in order to lock the connecting rod 200 received within the transversal U-shaped passage. The thread angle of the partial thread 23 has been adopted to allow a fast fixing action. Given the fact that the extension of the U-shaped passage 22 interferes with the extension of the through bore housing the locking insert 4, the locking force applied to the connecting rod 200 by means of the set-screw 5 is transmitted to the locking insert and also locks the relative orientation of the shank 3 with respect to the receiving head 2.

As discussed above, the distal extremity of the receiving head 2 includes a lateral rim surrounding the distal aperture 21, which is interrupted by the two opposite notches forming the U-shaped passage 22 and which has a circular inner periphery featuring the partial thread 23. The outer lateral periphery of the rim has a cross-section that is roughly rectangular in shape, with bevelled edges 25. The shorter sides of the lateral periphery exhibit, on their mid-section, a lateral longitudinal groove 26 going from the distal extremity of the receiving head 2 to the lateral aperture 42. The lateral longitudinal grooves 26, as will be apparent from the following description, are designed to allow the introduction of two pressing arms 101 of a dedicated locking instrument 100, the pressing arms traversing the grooves in order to act on the contact surface 41 of the locking insert 4. In other words, the grooves define longitudinal paths for the external pressing means represented by the pressing arms 101.

Each of the four bevelled edges 25 of the rim periphery is provided in its proximity with an indentation 24, which is designed to allow snap insertion of the locking instrument 100. These indentations 24 may have alternative shapes, for example, they may be notches, grooves or at least two holes.

The instrument 100 comprises two lateral prongs 103 that are intended to clamp the receiving head 2 acting on its shorter sides. The internal surface 102 of the prongs 103 presents a central removable rib 108 and four internally projecting pins 104 that are intended to cooperate with the indentations 24 of the receiving head 2 in order to assure a stable grip of the instrument 102 on the polyaxial pedicle screw 1, as clearly shown in FIG. 5. In other embodiments, a larger or smaller number of projecting pins 104 may be provided.

A central adjusting rod 106 is foreseen to press on the set screw 5 when the instrument 100 is used to clamp the pedicle screw of the present invention. This adjusting rod 106 is extended parallel to the arms prongs 103 and has a free end abutting on the fixing means 5. This feature allows implementing Minimal Invasive Surgery using the pedicle screw of the invention.

The pressing arms 101 are slidably mounted on the internal side of the prongs, and are designed in such a way that when the instrument 100 is attached to the receiving head 2 via the pins/indentations connection, they may slide within the longitudinal grooves 26 with their tips 102 pressing upon the contact surface 41 of the locking insert 4, keeping it in its locking position while still freely moving the rod and this is a great advantage if compared with the prior art solutions.

Figure 7:
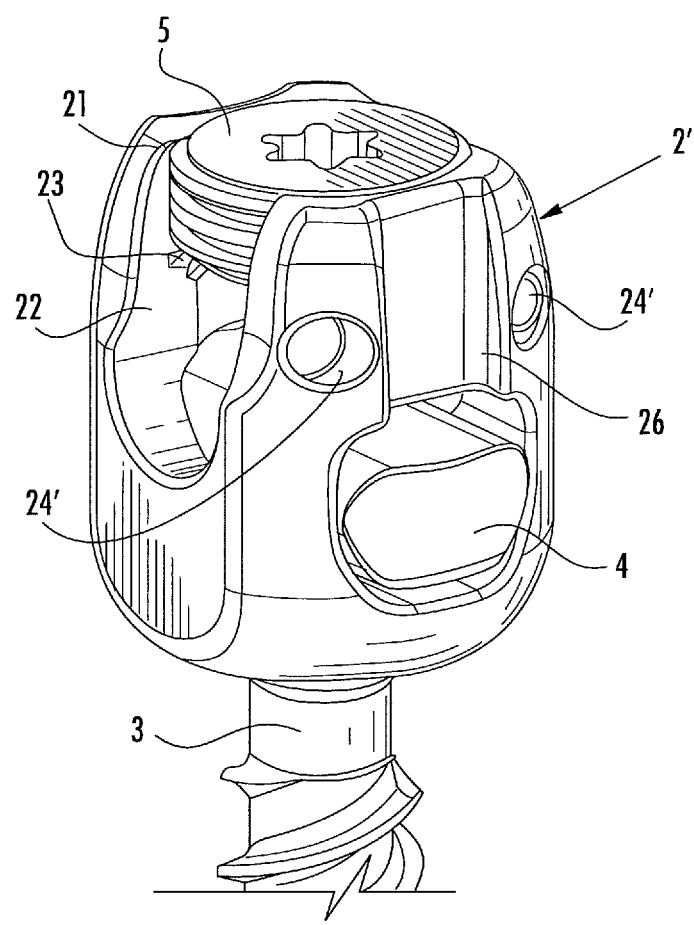
FIG. 7 shows a perspective view of another embodiment of the polyaxial pedicle screw, according to the present invention.
Figure 8:
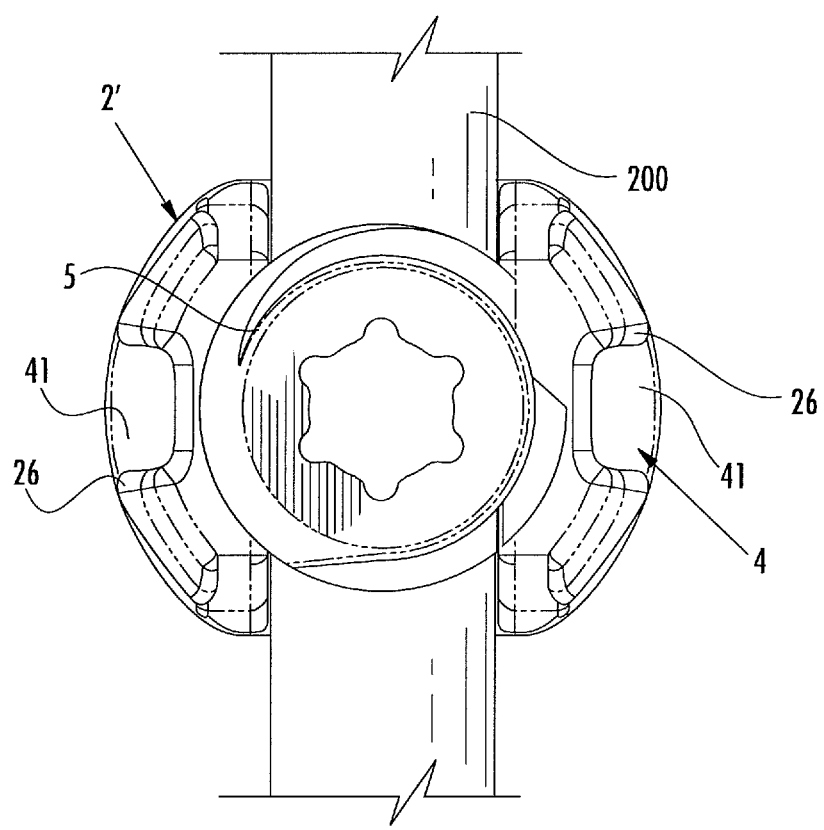
FIG. 8 shows a top view of the polyaxial pedicle screw of FIG. 7.
Figure 9:
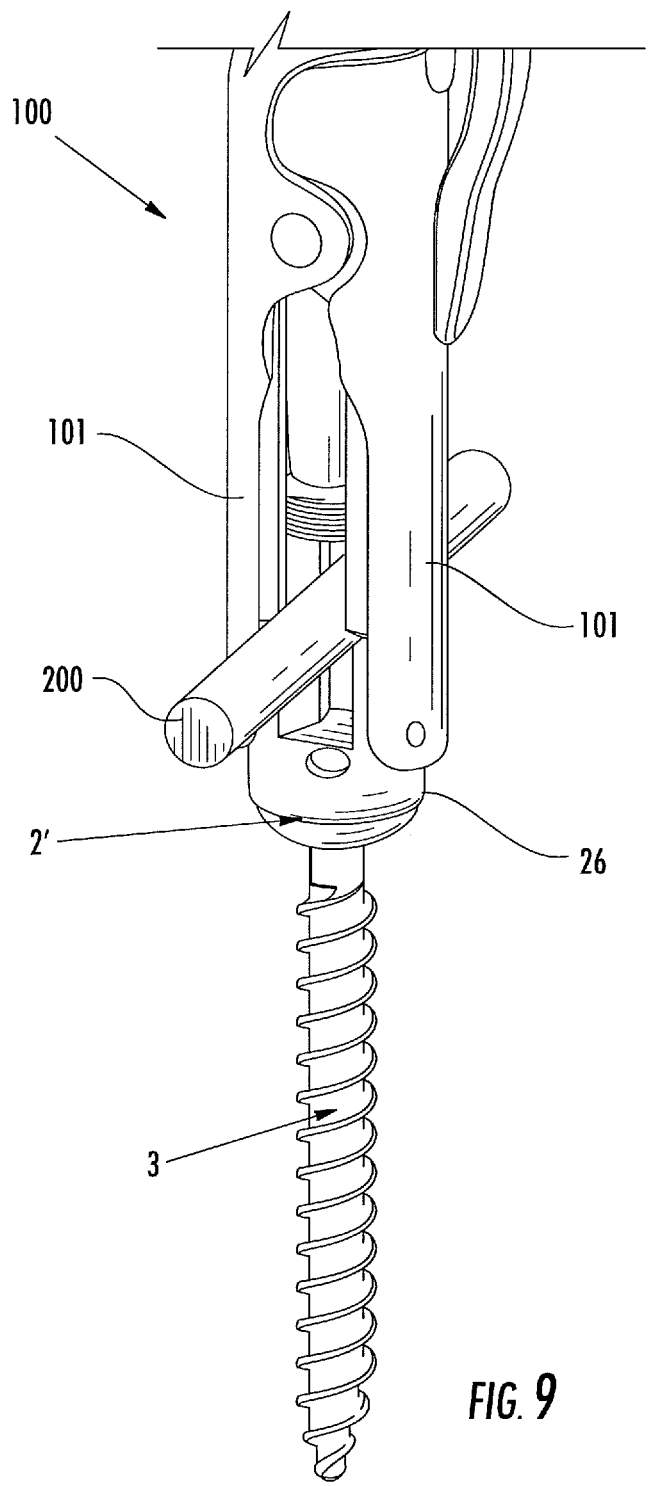
FIG. 9 shows a perspective view of the tip of an instrument adapted to act on the polyaxial pedicle screw according to the present invention and, in particular, on the embodiment shown in FIGS. 7 and 8.

Now, with more specific reference to the embodiments of the FIGS. 7, 8 and 9, it will be disclosed an alternative embodiment of the pedicle screw. All the components and the portions that are structurally identical of the previously disclosed embodiment will be identified with the same reference numbers.

The screw shown in FIG. 7 has a receiving head 2' with more rounded edges if compared with the receiving head 2 of the first embodiment. The lateral rim surrounding the distal aperture 21 is interrupted by the two opposite notches forming the U-shaped passage 22 and the inner internal periphery presents the partial thread 23. The outer lateral periphery of the rim has a cross-section that is roughly circular in shape, as shown in FIG. 8, with upper bevelled edges.

The opposite lateral longitudinal groove 26 are extended as in the previous embodiment from the distal extremity of the receiving head 2' to the lateral aperture 42 to allow the introduction of the two pressing arms 101 of the locking instrument 100, as shown in FIG. 9. The pressing arms 101 traverse both grooves 26 in order to act on the contact surface 41 of the locking insert 4. Differently from the first embodiment, the rim periphery is provided with indentations 24' which are located in a more central position with respect to the longitudinal extension receiving head 2', closer to the openings 42.

The fixation system comprising the polyaxial pedicle screw 1 according to the present invention may be implanted as follows. After completion of the preliminary surgical phases, the shank 3 of the polyaxial screw 1 is inserted in a pedicle location by introducing an appropriate wrench tip (which may be the dedicated instrument 100) within the socket 33. Then, the surgeon orientates the receiving head 2 or 2' in the desired angular relationship with the shank 3, possibly taking into account the position of neighboring polyaxial screws.

Now, by means of the pressing arms 101 of the locking instrument 100, it is possible to act on the locking insert 4 in order to lock the relative orientation of the receiving head 2 or 2'. Moreover, the adjusting rod 106 of the locking instrument 100 allows keeping in position the fixing means 5 without requiring a tight fixation of the pedicle screw 1.

The presence of the dedicated instrument does not prevent the insertion of a connecting rod received within the U-shaped passage 22. On the contrary, it is still possible to block the head of the pedicle screw 1 and adjust the rod 200 before fixing tight the fixing means 5. Therefore the surgeon may decide to insert such a rod 200 either when the orientation of the screw is locked or when the orientation is unlocked. Moreover, it is always possible to switch between the locked and the unlocked status of the device, notwithstanding the presence of a rod 200 within the U-shaped passage 22. For example, the rod 200 may be inserted with a locked screw, and should the surgeon notice that the receiving head 2 or 2' is not properly aligned with a neighboring receiving head, it is possible to unlock the screw to correct the error. This allows a distraction of two locked screws since they could also rotate to the final position.

Finally, when the surgeon is satisfied with the layout of the fixation system, he can lock the fixing means, such as the set-screw 5, in the distal aperture 21 for locking both the orientation of the receiving head 2 and the connecting rod 200. The instrument 100 may be safely removed after the final locking has been performed.

A person skilled in the art, in order to meet specific needs, will readily acknowledge the possibility of changes and variations to the polyaxial pedicle screw described above, all of which, however, are within the scope of protection as defined by the following claims. In this respect, the surface of all components such as the screw shaft, the screw head or the indentations grooves may be provided with a suitable roughness for improving gripping.

That which is claimed is:

1. A polyaxial pedicle screw comprising:
    a receiving body having a proximal end, and a distal end longitudinally opposed to the proximal end, the proximal end defining a proximal aperture, the distal end defining a distal aperture, a pair of lateral apertures, and a U-shaped passageway extending transversely and opening on a periphery of the distal aperture;
    a shank comprising a head rotatably carried within said receiving body, and a threaded portion extending from said head and through the proximal aperture external to said receiving body;
    a locking insert carried by said receiving body and being slidably inserted through the pair of lateral apertures and into a locked position for locking said head with respect to said receiving body, said locking insert having a contact surface being exposed through the pair of lateral apertures of said receiving body; and
    a nut threadingly engaging the distal end for locking a connecting rod to be received within said U-shaped passageway;
    the distal end of said receiving body comprising at least one longitudinal groove defining at least one longitudinal path extending from a topmost distal end of said receiving body and for a tool to contact said locking insert.

2. The polyaxial pedicle screw according to claim 1 wherein the tool acts on the contact surface to maintain said locking insert in the locked position; wherein said receiving body defines a throughbore transversely extending orthogonal to the U-shaped passageway between the pair of lateral apertures; and wherein said locking insert is carried within the throughbore.

3. The polyaxial pedicle screw according to claim 2 wherein the at least one longitudinal groove opens on said throughbore.

4. The polyaxial pedicle screw according to claim 2 wherein the throughbore is offset with respect to the U-shaped passageway.

5. The polyaxial pedicle screw according to claim 2 wherein the locking insert has an elongated shape and comprises a pair of lateral arms extending respectively through the pair of lateral apertures without projecting out of said receiving body, said pair of lateral arms defining the contact surface.

6. The polyaxial pedicle screw according to claim 5 wherein said pair of lateral apertures prevent motion of said pair of lateral arms of said locking insert in a distal direction.

7. The polyaxial pedicle screw according to claim 1 wherein said receiving body defines a plurality of tool receiving recesses on an external surface thereof.

8. The polyaxial pedicle screw according to claim 7 wherein the external surface of said receiving body includes a plurality of bevelled surfaces; and wherein the plurality of tool receiving recesses are adjacent at least one bevelled surface.

9. The polyaxial pedicle screw according to claim 1 wherein said contact surface is substantially flat.

10. The polyaxial pedicle screw according to claim 1 wherein said locking insert has a mating surface opposite to the contact surface and being concave.

11. A polyaxial pedicle screw comprising:
    a receiving body having a proximal end, and a distal end longitudinally opposed to the proximal end, the proximal and defining a proximal aperture, the distal end defining a pair of lateral apertures, and a passageway extending transversely;
    a shank comprising a head carried within said receiving body, and a threaded portion extending from said head and through the proximal aperture;
    a locking insert carried by said receiving body and being slidably inserted through the pair of lateral apertures and into a locked position for locking said head with respect to said receiving body; and
    a nut threadingly engaging the distal end for locking a connecting rod to be received within said passageway;
    the distal end of said receiving body comprising at least one longitudinal groove defining at least one longitudinal path extending from a topmost distal end of said receiving body and for a tool to contact said locking insert.

12. The polyaxial pedicle screw according to claim 11 wherein the tool acts on a contact surface of said locking insert to maintain said locking insert in the locked position; wherein said receiving body defines a throughbore transversely extending orthogonal to the passageway between the pair of lateral apertures; and wherein said locking insert is carried within the throughbore.

13. The polyaxial pedicle screw according to claim 12 wherein the locking insert has an elongated shape and comprises a pair of lateral arms extending respectively through the pair of lateral apertures without projecting out of said receiving body, said pair of lateral arms defining the contact surface.

14. The polyaxial pedicle screw according to claim 11 wherein said receiving body defines a plurality of tool receiving recesses on an external surface thereof.

15. A fixation system comprising:
    at least one polyaxial pedicle screw comprising
        a receiving body having a proximal end, and a distal end longitudinally opposed to the proximal end, the proximal end defining a proximal aperture, the distal end defining a distal aperture, a pair of lateral apertures, and a U-shaped passageway extending transversely and opening on a periphery of the distal aperture, a shank comprising a head rotatably carried within said receiving body, and a threaded portion extending from said head and through the proximal aperture external to said receiving body, a locking insert carried by said receiving body and being slidably inserted through the pair of lateral apertures and into a locked position for locking said head with respect to said receiving body, said locking insert having a contact surface being exposed through the pair of lateral apertures of said receiving body, and a nut threadingly engaging the distal end for locking a connecting rod to be received within said U-shaped passageway, the distal end of said receiving body comprising at least one longitudinal groove defining at least one longitudinal path extending from a topmost distal end of said receiving body and for a tool to contact said locking insert;

at least a connecting rod to be carried within the U-shaped passageway; and a locking tool to act on said contact surface.

16. The fixation system according to claim 15 wherein the tool acts on the contact surface to maintain said locking insert in the locked position; wherein said receiving body defines a throughbore transversely extending orthogonal to the U-shaped passageway between the pair of lateral apertures; and wherein said locking insert is carried within the throughbore.

17. The fixation system according to claim 16 wherein the locking insert has an elongated shape and comprises a pair of lateral arms extending respectively through the pair of lateral apertures without projecting out of said receiving body, said pair of lateral arms defining the contact surface.

18. The fixation system according to claim 15 wherein said receiving body defines a plurality of tool receiving recesses on an external surface thereof.

19. The fixation system according to claim 18 wherein said locking tool comprises a pair of lateral prongs for clamping said receiving body, and a plurality of pressing arms slidably coupled to said pair of lateral prongs.

20. The fixation system according to claim 19 wherein said pair of lateral prongs comprises a plurality of internally projecting pins for cooperating with the plurality of tool receiving recesses for securing said locking tool and said receiving body.

21. A fixation system comprising:
at least one polyaxial pedicle screw comprising
a receiving body having a proximal end, and a distal end longitudinally opposed to the proximal end, the proximal end defining a proximal aperture, the distal end defining a distal aperture, a pair of lateral apertures, and a U-shaped passageway extending transversely and opening on a periphery of the distal aperture, a shank comprising a head rotatably carried within said receiving body, and a threaded portion extending from said head and through the proximal aperture external to said receiving body, a locking insert carried by said receiving body and being laterally movable through the pair of lateral apertures and into a locked position for locking said head with respect to said receiving body, said locking insert having a contact surface being exposed through the pair of lateral apertures of said receiving body, and a nut threadingly engaging the distal end for locking a connecting rod to be received within said U-shaped passageway;

at least a connecting rod to be carried within the U-shaped passageway; and a locking tool to act on said contact surface and comprising a pair of lateral prongs for clamping said receiving body, and a plurality of pressing arms slidably coupled to said pair of lateral prongs;

said receiving body defines a plurality of tool receiving recesses on an external surface thereof.

* * * * *